US011457955B2

(12) United States Patent
Garcia et al.

(10) Patent No.: US 11,457,955 B2
(45) Date of Patent: Oct. 4, 2022

(54) COMPOUND PLATE FOR CRANIOTOMY CLOSURES

(71) Applicant: Zimmer Biomet CMF and Thoracic, LLC, Jacksonville, FL (US)

(72) Inventors: Saddy Garcia, St. Augustine, FL (US); Ryan N Luby, Ponte Vedra Beach, FL (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 92 days.

(21) Appl. No.: 16/874,096

(22) Filed: May 14, 2020

(65) Prior Publication Data

US 2020/0360058 A1 Nov. 19, 2020

Related U.S. Application Data

(60) Provisional application No. 62/848,993, filed on May 16, 2019.

(51) Int. Cl.
*A61B 17/68* (2006.01)
*A61B 17/80* (2006.01)

(52) U.S. Cl.
CPC ........ *A61B 17/688* (2013.01); *A61B 17/8061* (2013.01)

(58) Field of Classification Search
CPC ....... A61B 17/68; A61B 17/688; A61B 17/80; A61B 17/8061; A61F 2/2875
See application file for complete search history.

(56) References Cited

U.S. PATENT DOCUMENTS

| 5,201,737 | A | * | 4/1993 | Leibinger | A61B 17/688 606/280 |
| 5,468,242 | A | * | 11/1995 | Reisberg | A61B 17/8085 606/151 |
| 5,503,164 | A | * | 4/1996 | Friedman | A61B 17/8085 128/897 |
| 5,578,036 | A | * | 11/1996 | Stone | A61B 17/688 606/281 |
| 5,766,176 | A | * | 6/1998 | Duncan | A61B 17/8085 606/281 |
| 5,961,519 | A | * | 10/1999 | Bruce | A61B 17/8085 606/280 |

(Continued)

FOREIGN PATENT DOCUMENTS

WO WO-2020232240 A1 11/2020

OTHER PUBLICATIONS

"International Application Serial No. PCT US2020 032876, International Search Report dated Oct. 2, 2020", 7 pages.

(Continued)

*Primary Examiner* — Eric S Gibson
(74) *Attorney, Agent, or Firm* — Schwegman Lundberg & Woessner, P.A.

(57) ABSTRACT

Disclosed is a compound bone plate for attaching a bone flap to a skull. The compound bone plate can include a first plate member, a second plate member, a burr hole cover, and a strut. The first plate member can be operable to be attached to the bone flap and the skull. The second plate member can be operable to be attached to the bone flap and the skull. The strut can connect the first plate member, the second plate member, and the burr hole cover.

20 Claims, 6 Drawing Sheets

(56) References Cited

U.S. PATENT DOCUMENTS

| | | | | |
|---|---|---|---|---|
| 7,833,253 | B2* | 11/2010 | Ralph | A61B 17/688 606/283 |
| 9,463,046 | B2* | 10/2016 | Qwarnstrom | A61F 2/2875 |
| 10,076,416 | B2* | 9/2018 | Engstrand | A61F 2/28 |
| 10,232,169 | B2* | 3/2019 | Govea | A61N 1/0539 |
| 10,881,519 | B2* | 1/2021 | Engstrand | A61F 2/30965 |
| 10,898,332 | B2* | 1/2021 | Engstrand | A61F 2/2875 |
| 2004/0210224 | A1* | 10/2004 | Ahmad | A61B 17/688 606/916 |
| 2006/0287654 | A1* | 12/2006 | Posnick | A61B 17/688 606/279 |
| 2007/0173844 | A1* | 7/2007 | Ralph | A61B 17/688 606/916 |
| 2009/0076617 | A1* | 3/2009 | Ralph | A61B 17/688 623/17.19 |
| 2011/0054540 | A1* | 3/2011 | Ralph | A61B 17/688 606/283 |
| 2013/0053900 | A1* | 2/2013 | Qwarnstrom | A61F 2/2875 606/286 |
| 2015/0374497 | A1* | 12/2015 | Engstrand | A61B 17/688 623/17.19 |
| 2016/0143664 | A1 | 5/2016 | Garcia et al. | |
| 2017/0239054 | A1* | 8/2017 | Engstrand | A61B 17/688 |
| 2020/0360058 | A1* | 11/2020 | Garcia | A61B 17/8061 |
| 2021/0338286 | A1* | 11/2021 | Berg | A61B 17/686 |

OTHER PUBLICATIONS

"International Application Serial No. PCT US2020 032876, Written Opinion dated Oct. 2, 2020", 8 pages.

"International Application Serial No. PCT/US2020/032876, International Preliminary Report on Patentability dated Nov. 25, 2021", 14 pgs.

"European Application Serial No. 20729577.5, Response to Communication pursuant to Rules 161(1) and 162 EPC filed Jul. 6, 2022", 13 pgs.

\* cited by examiner

COMPOUND PLATE FOR CRANIOTOMY CLOSURES

CLAIM OF PRIORITY

This application claims the benefit of U.S. Provisional Patent Application Ser. No. 62/848,993, filed on May 16, 2019, the benefit of priority of which is claimed hereby, and which is incorporated by reference herein in its entirety.

FIELD OF THE DISCLOSURE

The present disclosure relates to surgical systems. Specifically, the present disclosure relates to assemblies and methods used in a craniotomy.

BACKGROUND

For certain neuro surgical procedures, a section of the skull is removed to access the brain. This section, known as a bone flap, allows surgeons access to the brain for treating tumors or trauma to the brain. Once a portion of the skull, known as a bone flap, is separated from the skull, it is placed at a sterile area while the surgeon operates on the brain. Upon completion of the procedure, the bone flap is replaced and secured to the skull.

To facilitate creation of the bone flap, one or more burr holes can be created. The burr holes provide a location for a surgeon to insert a saw or other cutting instrument into the skull to form a cut. For example, multiple burr holes can be drilled in the skull and then the surgeon can cut from one burr hole to another to form the bone flap. The cut can form a gap between the skull and the bone flap that has a maximum width of about 2 mm.

Currently, to secure the bone flap to the skull, the surgeon may use individual bone plates. However, current bone plates have numerous problems. First, current bone plates are small and difficult for a surgeon to handle within the surgical environment. For example, due to the small size of the current bone plates, there is a risk that they could slip from the surgeon's hand and fall into the cranial cavity. In addition, there is a risk of the current bone plates snagging otherwise binding with screws used to fasten them to the skull and bone flap. Should this happen, the current bone plates can spin at a high RPM and cause injury such as cuts, torn surgical gloves, chipping of the patient's skull, etc.

The compound bone plates disclosed herein reduce or eliminate the problems disclosed above, which were discovered by the inventors of the present disclosure.

SUMMARY

To better illustrate the systems and methods disclosed herein, a non-limiting list of summary is provided here:

A compound bone plate for attaching a bone flap to a skull is disclosed herein. The compound bone plate can comprise a first plate member, a second plate member, a burr hole cover, and a strut. The first plate member can be operable to be attached to the bone flap and the skull. The second plate member can be operable to be attached to the bone flap and the skull. The strut can connect the first plate member, the second plate member, and the burr hole cover.

A compound bone plate for attaching a bone flap to a skull is disclosed herein. The compound bone plate can comprise a plurality of plate members, a plurality of burr hole covers, and a strut. Each of the plurality of plate members can be operable to be attached to the bone flap and the skull. The strut can connect the plurality of plate members and burr hole covers.

A method for performing a craniotomy is disclosed herein. The method can comprise: drilling at least one burr hole in a skull; cutting the skull at the burr hole to create a bone flap; removing the bone flap from the skull; attaching a first portion of a bone plate assembly to the bone flap; placing the bone flap into an opening formed when the bone flap was removed from the skull; and attaching a second portion of the bone plate assembly to the skull. The bone plate assembly can include a first plate member, a second plate member, a burr hole cover, and a strut connecting the first plate member, the second plate member, and the burr hole cover.

BRIEF DESCRIPTION OF THE FIGURES

The above-mentioned and other features and advantages of this disclosure, and the manner of attaining them, will become more apparent and the disclosure itself will be better understood by reference to the following description of embodiments taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure any manner.

DETAILED DESCRIPTION

For certain neurosurgical procedures, a section of the skull is removed to access the brain. These sections can vary in size depending on how much access surgeons need for treating tumors or trauma to the brain. During surgery, surgeons can use a sterile ink marker to first outline a cutline at the area where access is needed. A burr hole can be created for giving a bone saw initial access to cut along the cutline. In some cases, more than one burr hole is created. After the burr holes are created, the bone saw can be used to cut from burr hole to burr hole.

Once the bone flap is separated from the skull, it can then be removed and placed in a sterile area while the surgeon operates on the brain. Upon completion of the procedure, the bone flap is replaced and multiple plates and screws can be used to secure the bone flap to the skull. The plates, sometimes referred to as plate members, can be small and difficult to hold while driving screws to fasten the plates to the skull and bone flap.

The assemblies and methods disclosed herein address the difficulty in holding bone plates by compounding the different plates needed into one plate. For instance, as disclosed herein, multiple bone plates can be connected using one or more struts so as to give surgeons more surface area in which to grip during the driving of the screws or other suitable fasteners. Also, because of this one-piece, or compound, design, the plate itself also can be used as a stencil for surgeons to outline the cutlines needed for the selected compound implant.

As disclosed herein, a compound bone plate can include one or more plate members that can be joined together by a strut. The compound bone plate also can include one or more burr hole covers. The burr hole covers also can act as plate members and can be used to help secure the bone flap to the skull. The strut can be rigid or flexible to allow the surgeon flexibility in determining a shape of the bone flap.

Figure 1:
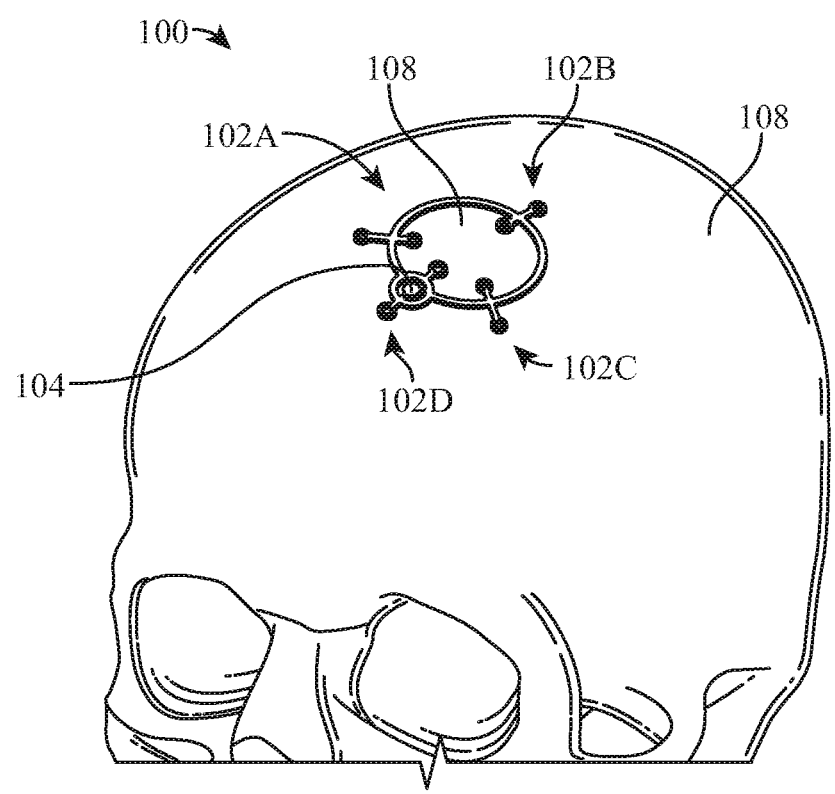
FIG. 1 shows a skull and a compound bone plate in accordance with at least one example of the present disclosure.

Turning now to the figures, FIG. 1 shows circular compound bone plate 100 in accordance with at least one example of the present disclosure. Compound bone plate 100 can include one or more plate members such as a first plate member 102A, a second plate member 102B, a third plate member 102C, and a fourth plate member 102D (collectively plate members 102). Compound bone plate 100 also can include one or more burr hole covers 104. As shown in FIG. 1, fourth plate member 102D and burr hole cover 104 can be combined to form a single structure.

During surgery, compound bone plate 100 can be placed against a skull 106. While placed against skull 106, compound bone plate 100 can be used as a stencil so that a surgeon can trace an outline showing where cuts can be made in skull 106 so that a bone flap 108 can be removed. Burr hole cover 104 can also be traced around to show where burr holes are to be drilled into skull 106.

Figure 2:
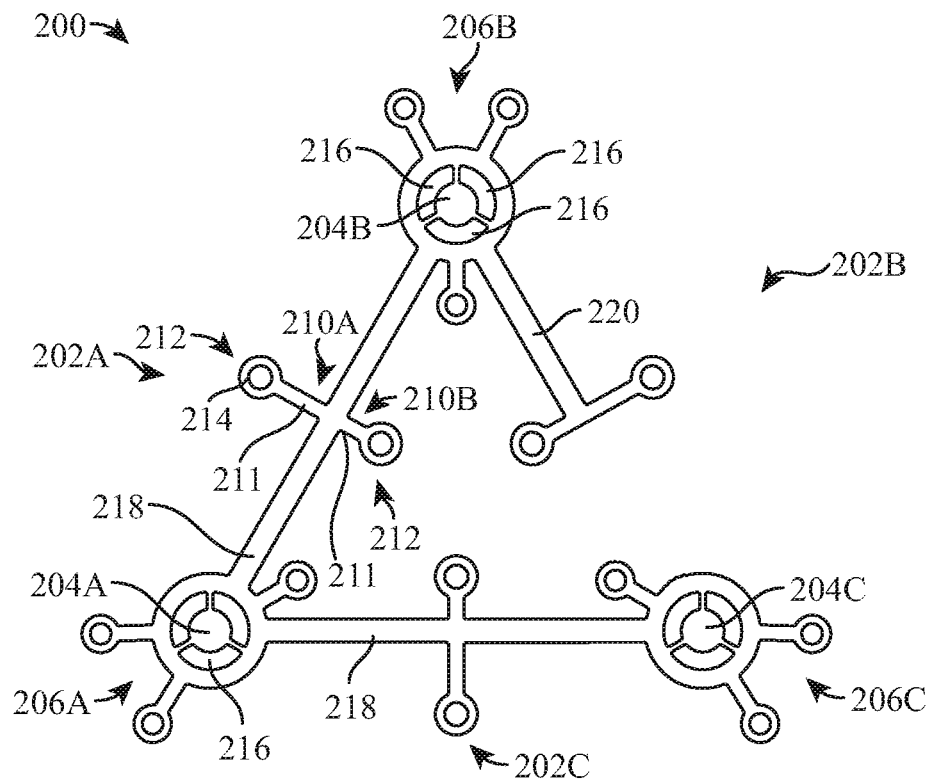
FIG. 2 shows a compound bone plate in accordance with at least one example of the present disclosure.

FIG. 2 shows a triangular compound bone plate 200 in accordance with at least one example of the present disclosure. Compound bone plate 200 can include a first plate member 202A, a second plate member 202B, and a third plate member 202C (collectively bone plate members 202). Compound bone plate 200 also can include a first burr hole cover 204A, a second burr hole cover 204B, and a third burr hole cover 204C (collectively burr hole covers 204). As shown in FIG. 2, plate members and burr hole covers can be combined into a single structure, such as a first bone plate/burr hole cover 206A, a second bone plate/burr hole cover 206B, and a third bone plate/burr hole cover 206C (collectively, bone plate/burr hole covers 206).

Figure 3A:
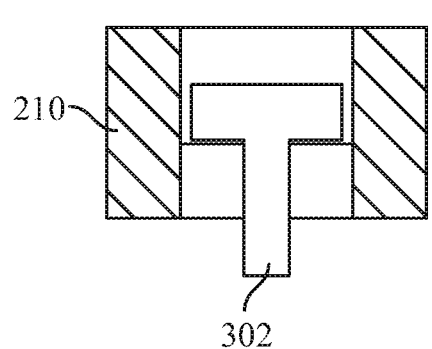
FIGS. 3A and 3B show portions of a plate member in accordance with at least one example of the present disclosure.
Figure 3B:
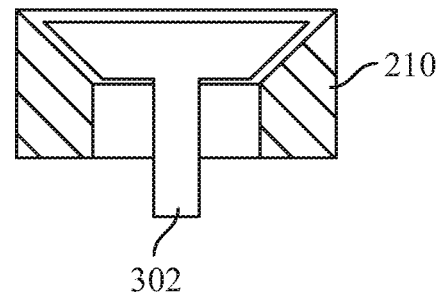

One or more bone plate members 202 and bone plate/burr hole covers 206 each can include prongs 210A and 210B that include a first portion 211 and a second portion 212. As shown in FIG. 2, one of the prongs (210B) can project into an interior defined by compound bone plate 200 and one of the prongs (210A) can project out of the interior into an exterior portion defined by compound bone plate 200. First portion 210 can define a hole 214. Hole 214 can be sized to receive a screw 302 (see FIGS. 3A and 3B) for securing plate members 202 and bone plate/burr hole covers 206 to a bone flap, such as bone flap 108, and a skull, such as skull 106. Hole 214 can include a recess having a rectangular profile as shown in FIG. 3A or a beveled profile as shown in FIG. 3B that can allow screw 302 or other fasteners to be recessed into the plate members 202. Recessing screw 302 can help with comfort for a patient by preventing screw 302 from contacting the scalp and/or causing bumps or other protrusions in the scalp.

As shown in FIG. 2, one or more bone plate/burr hole covers 206 can define one or more openings 216. Openings 216 can be utilized by a surgeon to mark skull 106. For example, during surgery, the surgeon can use a marking instrument, such as a pen, marker, or awl, to scribe an outline of one or more of burr hole covers 204. Once the outlines are scribed, the surgeon can remove compound bone plate 200 and drill burr holes using the scribed outlines.

Compound bone plate 200 also can include a strut 218. As disclosed herein, strut 218 can connect plate members 202 and bone plate/burr hole covers 206 to one another. As shown in FIG. 2, strut 218 can be divided into segments separated by bone plate/burr hole covers 206. In addition, one of the segments can be divided into a first section 220 and a second section 222. By having one of the segments 218 divided, compound bone plate 200 can be pliable thus allowing compound bone plate 200 to be bent into various shapes or expanded as needed during surgery. In addition, the flexible nature of compound bone plate 200, or any compound bone plate disclosed herein, allows the surgeon to manipulate compound bone plate 200 to account for cuts that may not be straight or do not exactly follow stencil.

As disclosed herein, one or more plate members 202 can be sized so that once the skull is cut, plate members 202 can have the same extension on each side of the cut. One or more burr hole covers 204 and bone plate/burr hole covers 206 can be sized the same way. For example, when compound bone plate 200, or any compound bone plate disclosed herein, is used as a stencil for defining a shape and size of a bone flap, the surgeon may draw and cut on one side (e.g., the interior of compound bone plate 200) of strut 218. As a result, first portion 211 of prong 210A can be longer than first portion 211 of prong 210B so that holes 214 are spaced an equal distance from the cut made in the skull.

Figure 4:
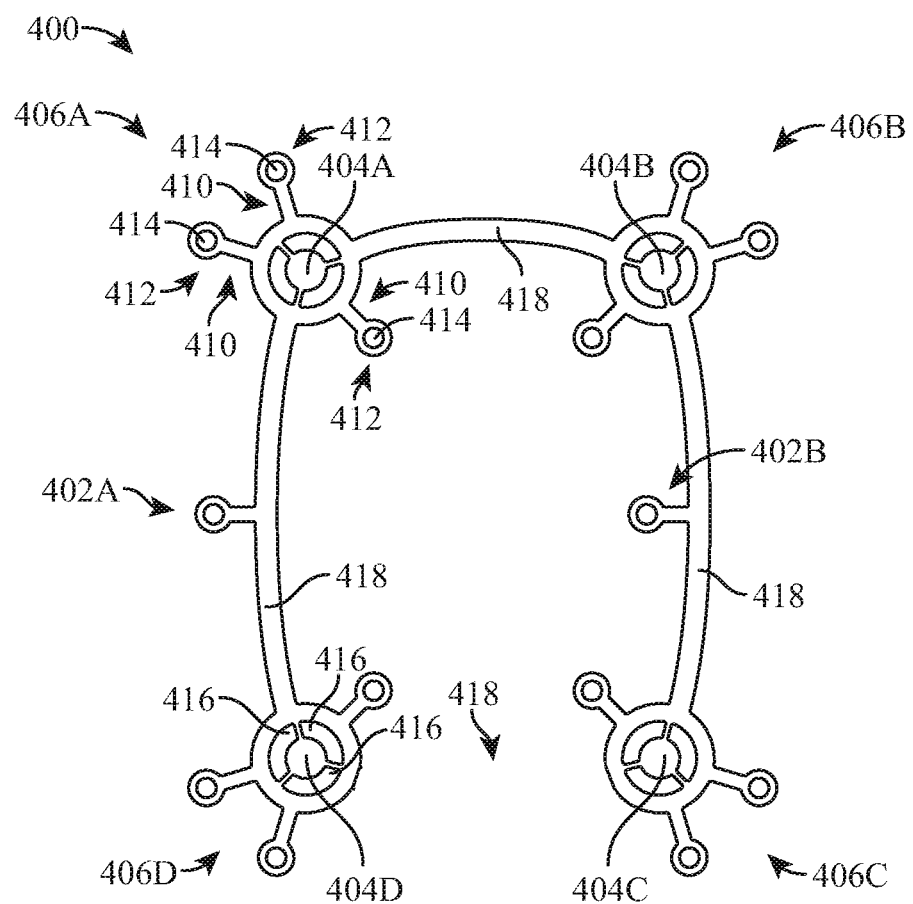
FIG. 4 shows a compound bone plate in accordance with at least one example of the present disclosure.

FIG. 4 shows a rectangular compound bone plate 400 in accordance with at least one example of the present disclosure. Compound bone plate 400 can include a first plate member 402A and a second plate member 402B (collectively bone plate members 402). As shown in FIG. 4, bone plate members 402 can be located on one side of a strut 418. For example, a bone plate member can be positioned such that it projects into an interior defined by struts 418 as shown by bone plate member 402B. A bone plate member can also be positioned such that it projects out of the interior defined by struts 418 as shown by bone plate member 402A. In this manner, first plat member 402A and/or second plate member 402B can aid in correctly orienting the bone flap when it is replaced. For example, the surgeon can make a note that first plate member 402A and/or second plate member 402B are located on his/her left when the stencil is created. When replacing the bone flap, the surgeon can again make sure first plate member 402A and second plate member 402B are locate on his/her left, thus ensuring the bone flat is placed correctly into the skull. While FIG. 4 shows struts 418 having a single bone plate member, multiple bone plate members can be located along a single strut.

Compound bone plate 400 also can include one or more burr hole covers, such as a first burr hole cover 404A, a second burr hole cover 404B, a third burr hole cover 404C, and a fourth burr hole cover 404D (collectively burr hole covers 404). As shown in FIG. 4, plate members and burr hole covers can be combined into a single structure, such as a first bone plate/burr hole cover 406A, a second bone plate/burr hole cover 406B, a third bone plate/burr hole cover 406C, and a fourth bone plate/burr hole cover 406D (collectively, bone plate/burr hole covers 406).

One or more bone plate members 402 and bone plate/burr hole covers 406 each can include one or more arms, such as a first portion 410 and a second portion 412. Second portion 412 can define a hole 414. Hole 414 can be sized to receive screw 302 as described herein and shown in FIGS. 3A and 3B. As disclosed herein, holes 414 and screws 302 can be used to secure one or more plate members 402 and bone plate/burr hole covers 406 to a bone flap and a skull.

As shown in FIG. 4, one or more of bone plate/burr hole covers 406 can define one or more openings 416. Openings 416 can be utilized by a surgeon to mark skull 106. For example, during surgery, the surgeon can use a marking instrument, such as a pen, marker, or awl, to scribe an outline of one or more of burr hole covers 404. Once the outlines are scribed, the surgeon can remove compound bone plate 400 and drill burr holes using the scribed outlines.

Compound bone plate 400 also can include a strut 418. As disclosed herein, strut 418 can connect one or more of plate members 402 and bone plate/burr hole covers 406 to one another. As shown in FIG. 4, strut 418 can be divided into segments and one of the segments can be divided into a first section 420 and a second section 422. By having one of struts 418 divided, compound bone plate 400 can be pliable thus allowing compound bone plate 400 to be bent into various shapes or expanded as needed during surgery.

Figure 5:
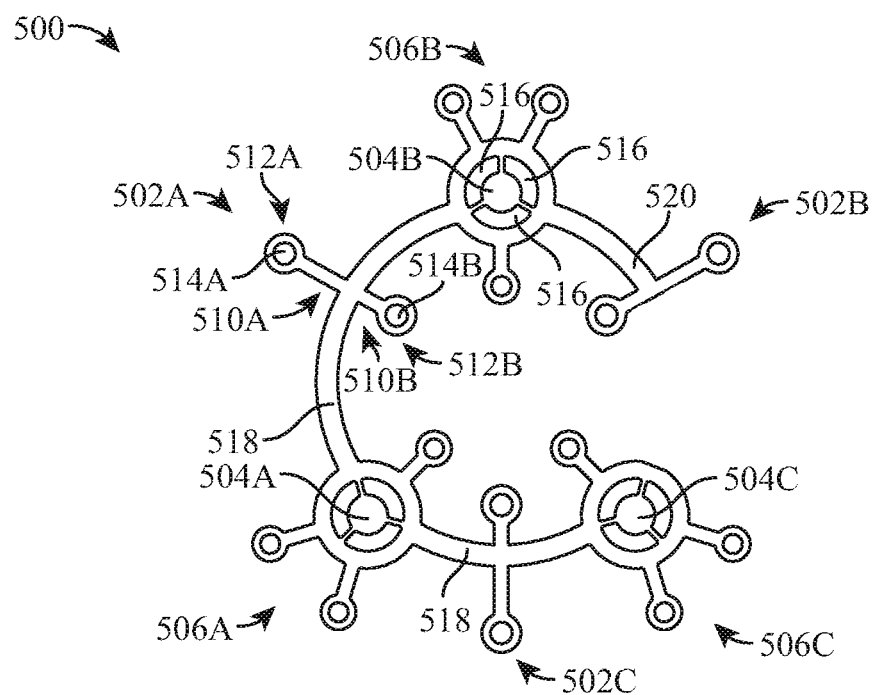
FIG. 5 shows a compound bone plate in accordance with at least one example of the present disclosure.

FIG. 5 shows a circular compound bone plate 500 in accordance with at least one example of the present disclosure. Compound bone plate 500 can include a first plate member 502A, a second plate member 502B, and a third plate member 502C (collectively bone plate members 502).

Compound bone plate 500 also can include a first burr hole cover 504A, a second burr hole cover 504B, and a third burr hole cover 504C (collectively burr hole covers 504). As shown in FIG. 5, one or more of plate members and burr hole covers can be combined into a single structure, such as a first bone plate/burr hole cover 506A, a second bone plate/burr hole cover 506B, and a third bone plate/burr hole cover 506C (collectively, bone plate/burr hole covers 506).

One or more bone plate members 502 and bone plate/burr hole covers 506 each can include prongs that include a first portion 510 and a second portion 512. First portion 510 can define a hole 514. Hole 514 can be sized to receive screw 302 as described herein and shown in FIGS. 3A and 3B. As disclosed herein, holes 514 and screws 302 can be used to secure plate members 502 and bone plate/burr hole covers 506 to a bone flap and a skull. As shown in FIG. 5, first portion 510 and second portion 512 of bone plate members 502 can be different sizes. For instance, first portion 510A projecting out of an interior defined by struts 518 can be longer than first portion 510B that projects into the interior defined by struts 518.

As shown in FIG. 5, one or more of bone plate/burr hole covers 506 can define one or more openings 516. Openings 516 can be utilized by a surgeon to mark skull 106. For example, during surgery, the surgeon can use a marking instrument, such as a pen, marker, or awl, to scribe an outline of one or more of burr hole covers 504. Once the outlines are scribed, the surgeon can remove compound bone plate 500 and drill burr holes using the scribed outlines.

Compound bone plate 500 also can include a strut 518. As disclosed herein, strut 518 can connect one or more of plate members 502 and bone plate/burr hole covers 506 to one another. As shown in FIG. 5, one of the segments can divided removed. By having one of segments removed, compound bone plate 500 can be pliable thus allowing compound bone plate 500 to be bent into various shapes or expanded as needed during surgery.

Figure 6A:
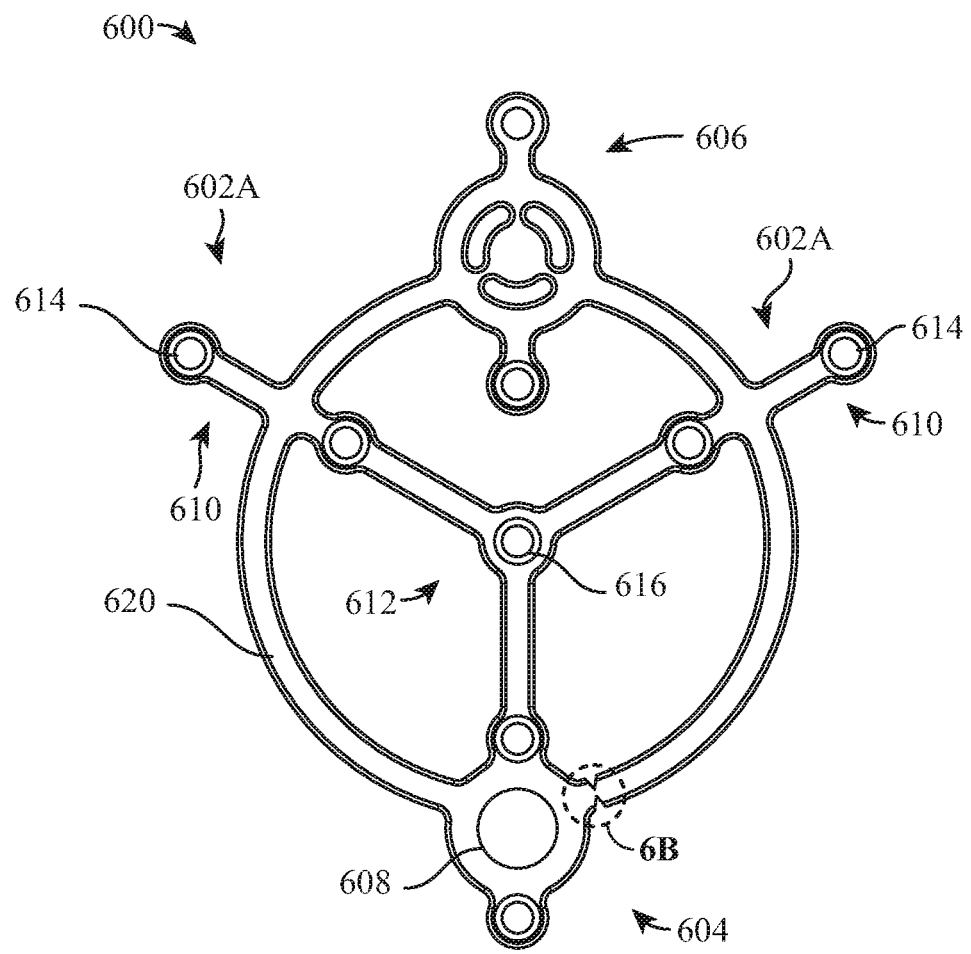
FIG. 6A shows a compound bone plate in accordance with at least one example of the present disclosure.

FIG. 6A shows a circular compound bone plate 600 in accordance with at least one example of the present disclosure. Compound bone plate 600 can include a first plate member 602A and a second plate member 602B (collectively bone plate members 602). Compound bone plate 600 also can include a bone plate/burr hole cover 606. Compound bone plate 600 can include a plate member 604 that includes a hole 608.

As disclosed herein, one or more bone plate members 602 and bone plate/burr hole covers 606 each can include prongs that include a first portion 610 and a second portion 612. First portion 610 can define a hole 614. Hole 614 can be sized to receive screw 302 as described herein and shown in FIGS. 3A and 3B. As disclosed herein, holes 614 and screws 302 can be used to secure plate members 602 and bone plate/burr hole covers 606 to a bone flap and a skull. As shown in FIG. 6A, second portion 612 can connect various bone plate members 602, bone plate member 504, and bone plate/burr hole covers 606 to one another. Second portion 612 can also include a hole 616 located at a center of compound bone plate 600.

Hole 616 can allow a surgeon to secure compound bone plate 600 to the patient's skull at a single location and rotate compound bone plate 600 around the center of compound bone plate 600. Having compound bone plate 600 be rotatable provides an advantage in that hole 608 can be used in cutting the patient's skull. For example, a router or other skull cutting instrument can be passed through hole 608 and compound bone plate 600 can be rotated as indicated by arrow 618 such that hole 608 allows the router or other cutting instrument to cut a perfect or near perfect circular bone flap. Upon cutting the bone flap, other holes defined by bone plate member 602, 604, and bone plate/burr hole covers 606 can be used to secure compound bone plate 600 to both the bone flap and the patient's skull upon completion of the surgical procedure.

Compound bone plate 600 also can include a strut 620. As disclosed herein, strut 620 can connect one or more of plate members 602, 604 and bone plate/burr hole covers 606 to one another. Strut 620 can allow compound bone plate 600 to be used as a stencil as disclosed herein.

Figure 6B:
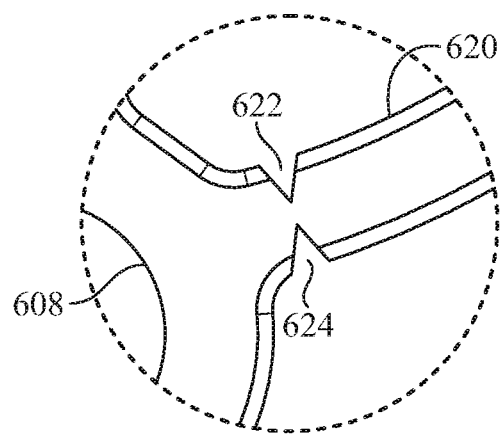
FIG. 6B shows a detail of a bone plate in accordance with at least one example of the present disclosure.

FIG. 6B shows a detail of compound bone plate 600. As shown in FIG. 6B, strut 620 can include a first notch 622 and a second notch 624. While FIG. 6B shows first notch 622 and second notch 624 located proximate plate member 604, notches, such as first notch 622 and second notch 624 may located proximate or adjacent to each of the plate members, bone plate/burr hole covers, or other components of a compound bone plate disclosed herein.

Consistent with the various embodiments disclosed herein, notches can have a "v" shape or other shape that results in a thinning of a strut, such as strut 620 as shown in FIG. 6B. The notches can allow the surgeon to cut the strut and remove potions of the strut that are initially used to connect the various components of a compound bone plate to one another.

The bone plate assemblies disclosed herein can be constructed of metals, polymers, ceramics, or combinations thereof. In addition, the bone plate assemblies can be constructed using various manufacturing methods, including, but not limited to, stamping, pressing, overmolding, etc. For example, the struts and plate members can be constructed of a metal, such as stainless steel or titanium. The metal billet can be stamped to create the basic shape of the bone plate assemblies including any holes needed therein.

Stated another way, the bone plate assemblies can be monolithic and stamped, pressed, etc. from a single piece of metal. Once the basic shape is created, the metal structure can be overmolded with a polymer so as to cover any sharp edges of the metal structure. In another example, the bone plate assemblies can be constructed entirely of a polymer and injection molded into a desired shape, such as a triangle shown in FIG. 2, a rectangular pattern as shown in FIG. 4, or a circle as shown in FIG. 5. While FIGS. 2, 4, 5, and 6 show bone plate assemblies that are symmetric (e.g., rectangles, circles, elliptical, equilateral triangles, oval, pentagonal, square, etc.), bone plate assemblies can be asymmetric and the bone plate members and burr hole covers can be arranged in asymmetrical patterns. In still another example, the various plate members, burr hole covers, struts, etc. can be made as individual pieces and assembled, either at a factory by a manufacturer or in an operating room by a surgeon.

As disclosed herein, the various compound bone plates disclosed herein can be manufactured from materials such as metals and polymers. Non-limiting examples of suitable materials can include, titanium and polyether ether ketone (PEEK). The various compound bone plates disclosed herein can have a thickness of about 20 to 30 thousandths of an inch. The thin nature of the various compound bone plates can allow for the compound bone plates to be bent so as to conform to a curvature or other irregularities of a patient's skull.

One or more of the various compound bone plates disclosed herein can also be included in a sterile kit or system that can include screws for attaching the compound bone plates to a patient's skull. For example, multiple compound bone plates can be included as a system that includes screws already partially attached to the compound bone plates. Each of the compound bone plates can be different sizes and shapes as disclosed herein. Thus, during surgery, the surgeon can select a compound bone plate that has the appropriate size and shape as needed for the patient's condition. The screws can be from about 4 mm long to about 5 mm long.

In addition, the bone plates assemblies disclosed herein can be components of a system. The system can include a plurality of bone plate assemblies. Each of the plurality of bone plate assemblies can be a different size and/or shape from other bone plate assemblies within the system. For example, the systems can include various bone plate assemblies that are different sizes, yet have the same basic shape, number of burr hole covers, plate members, etc. with the same basic arrangement. In another example, the systems can include various bone plate assemblies that are different sizes, and have different basic shapes (circular, rectangular, etc.) with different numbers of burr hole covers, plate members, etc. with different arrangements. As such, during surgery, a surgeon can select the appropriate compound bone plate for the patient's skull size as well as the geometry of the hole needed to access the brain.

Figure 7:
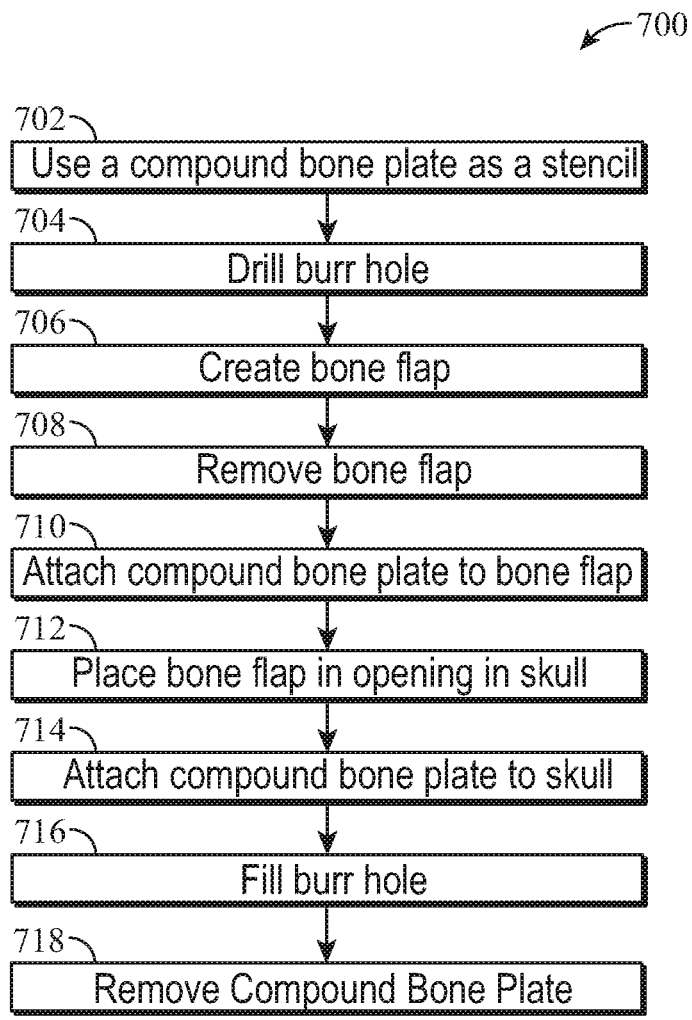
FIG. 7 shows an example method for performing a craniotomy in accordance with at least one example of the present disclosure.
Figure 8:
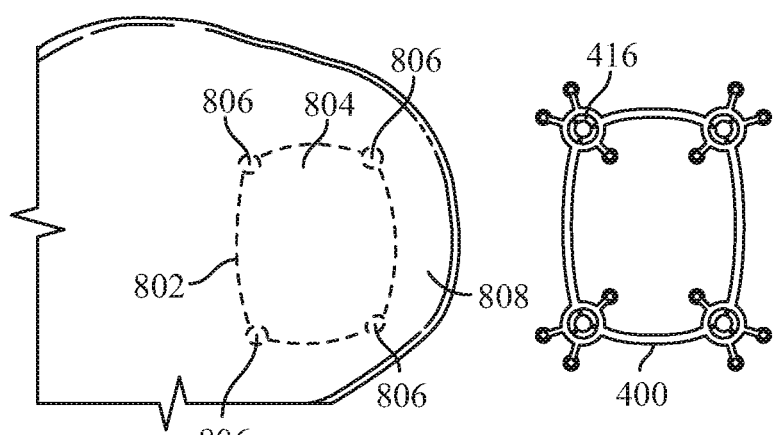
FIG. 8 shows an example craniotomy site in accordance with at least one example of the present disclosure.

FIG. 7 shows an example method 700 for performing a craniotomy in accordance with at least one example of the present disclosure. Method 700 can begin at stage 702 where a compound bone plate, such as compound bone plate 200, 400, 500, or 600, may be used as a stencil. For example, as shown in FIG. 8, compound bone plate 400 can be used to trace an outline 802 of a bone flap 804 and burr holes 806 onto a skull 808.

After outline 802 has been created, method 700 can proceed to stage 704 where burr holes 806 can be drilled into skull 808. From stage 704 method 700 can proceed to stage 706 where bone flap 804 can be cut. For example, as disclosed herein, once burr holes 806 are drilled a saw can be used to cut along outline 802 between burr holes 806.

Once skull 808 has been cut, bone flap 804 can be removed from skull 808 in stage 708. Removal of bone flap 804 can allow the surgeon to access the brain. Once the brain is accessible, the craniotomy can be performed. After the craniotomy is performed, compound bone plate 400 can be attached to bone flap 804 in stage 710 using screws 302. Once compound bone plate 400 is attached to bone flap 804, bone flap 804 can be placed in the opening in skull 808 created when bone flap 804 was removed from skull 808. By attaching compound bone plate 400 to bone flap 804 prior to placing bone flap 804 in the opening, compound bone plate 400 can prevent bone flap 804 from falling into the cranial cavity and/or otherwise contacting the brain.

Still consistent with embodiments disclosed herein, compound bone plate 400 can be attached to bone flap 804 before bone flap 804 is removed from skull 808. By attaching compound bone plate 400 to bone flap 804 before cutting skull 808 with a cranial saw, compound bone plate 400 can prevent bone flap 804 from falling into the cranial cavity and/or otherwise contacting the brain during cutting of skull 808.

From stage 712 method 700 can proceed to stage 714 where compound bone plate 400 can be attached to skull 808. For example, screws 302 can be used to attach second portion 412 of compound bone plate 400 to skull 808. Once bone flap 804 is attached to skull 808, burr holes 806 can be filled in stage 716. For example, a fill material can be injected into burr holes 806 via openings 416. Examples of the fill material can include, but are not limited to, CopiOs® bone void filler manufactured by ZIMMER BIOMET® of Warsaw, Ind., naOss® bone void filler manufactured by RTI SURGICAL® of Marquette, Mich.

From stage 714 method 700 can proceed to stage 716 where compound bone plate 400 can be removed from skull 808. Stage 716 can be performed at a later date after the craniotomy once skull 808 has had a chance to heal. While stage 716 can be performed, stage 716 does not have to be performed. For instance, compound bone plate 400 may be left attached to skull 808 indefinitely. Leaving compound bone plate 400 attached to skull 808 can minimize risks to the patient associated with subjected the patient to a second surgery to remove compound bone plate 400.

EXAMPLES

Example 1 is a compound bone plate for attaching a bone flap to a skull, the compound bone plate comprising: a first plate member operable to be attached to the bone flap and the skull; a second plate member operable to be attached to the bone flap and the skull; a burr hole cover; and a strut connecting the first plate member, the second plate member, and the burr hole cover.

In Example 2, the subject matter of Example 1 optionally includes wherein the burr hole cover defines one or more through holes sized to allow a bone fill material to pass through the burr hole cover and into a burr hole formed in the skull.

In Example 3, the subject matter of any one or more of Examples 1-2 optionally include wherein the first plate member and the burr hole cover are integrated as a single component.

In Example 4, the subject matter of anyone or more of Examples 1-3 optionally include wherein the strut is metallic and includes a polymer coating.

In Example 5, the subject matter of any one or more of Examples 1-4 optionally include wherein the first plate member comprises: a first prong operable to be attached to the bone flap; a second prong operable to be attached to the skull; and a third prong operable to be attached to the skull.

In Example 6, the subject matter of any one or more of Examples 1-5 optionally include wherein the strut orients the first plate member, the second plate member, and the burr hole cover in an asymmetric arrangement.

In Example 7, the subject matter of any one or more of Examples 1-6 optionally include wherein the strut orients the first plate member, the second plate member, and the burr hole cover in a symmetric arrangement.

In Example 8, the subject matter of any one or more of Examples 1-7 optionally include wherein the strut forms a circular or elliptical pattern.

In Example 9, the subject matter of any one or more of Examples 1-8 optionally include wherein the strut comprises four segments that form a rectangular pattern.

In Example 10, the subject matter of Example 9 optionally includes wherein the burr hole cover is located at an intersection of two of the four segments.

In Example 11, the subject matter of any one or more of Examples 9-10 optionally include wherein the first plate member, the second plate member, and the burr hole cover are attached to different segments of the four segments.

In Example 12, the subject matter of any one or more of Examples 9-11 optionally include wherein one of the four segments is divided into two-sub-segments.

In Example 13, the subject matter of any one or more of Examples 1-12 optionally include wherein the strut comprises three segments that form a triangular pattern.

In Example 14, the subject matter of Example 13 optionally includes wherein the burr hole cover is located at an intersection of two of the three segments.

In Example 15, the subject matter of any one or more of Examples 13-14 optionally include wherein the first plate member, the second plate member, and the burr hole cover are attached to different segments of the three segments.

In Example 16, the subject matter of any one or more of Examples 13-15 optionally include wherein one of the three segments is divided into two-sub-segments.

In Example 17, the subject matter of any one or more of Examples 1-16 optionally include wherein the strut comprises: a first strut member having a first end and a second end, the first plate member located in between the first end and the second end; and a second strut member having a third end and a fourth end, the second plate member located in between the third end and the fourth end.

In Example 18, the subject matter of Example 17 optionally includes wherein the burr hole cover joins the first strut member to the second strut member.

In Example 19, the subject matter of any one or more of Examples 1-18 optionally include wherein the compound bone plate is one of a plurality of bone plate assemblies, each of the bone plate assemblies are different sizes.

In Example 20, the subject matter of any one or more of Examples 1-19 optionally include wherein the compound bone plate is one of a plurality of bone plate assemblies, wherein the first plate member, the second plate member, and the burr hole cover for each of the plurality of bone plate assemblies has a different arrangement.

Example 21 is a compound bone plate for attaching a bone flap to a skull, the compound bone plate comprising: a plurality of plate members, each of the plurality of plate members operable to be attached to the bone flap and the skull; a plurality of burr hole covers; and a strut connecting the plurality of plate members and burr hole covers.

In Example 22, the subject matter of Example 21 optionally includes wherein each of the burr hole covers defines one or more through holes sized to allow a bone fill material to pass through the burr hole cover and into a burr hole formed in the skull.

In Example 23, the subject matter of any one or more of Examples 21-22 optionally include wherein at least one of the plurality of plate members and at least one of the plurality of burr hole covers are integrated as a single component.

In Example 24, the subject matter of any one or more of Examples 21-23 optionally include wherein the strut is metallic and includes a polymer coating.

In Example 25, the subject matter of any one or more of Examples 21-24 optionally include wherein at least one of the plate members comprises: a first prong operable to be attached to the bone flap; and a second prong operable to be attached to the skull; and a third prong operable to be attached to the skull.

In Example 26, the subject matter of any one or more of Examples 21-25 optionally include wherein the strut orients the plurality of plate members and the plurality of burr hole covers in an asymmetric arrangement.

In Example 27, the subject matter of any one or more of Examples 21-26 optionally include wherein the strut orients the plurality of plate members and the plurality of burr hole covers in a symmetric arrangement.

In Example 28, the subject matter of any one or more of Examples 21-27 optionally include wherein the strut forms a circular or elliptical pattern.

In Example 29, the subject matter of any one or more of Examples 21-28 optionally include wherein the strut comprises four segments that form a rectangular pattern.

In Example 30, the subject matter of Example 29 optionally includes wherein at least one of the plurality of burr hole covers is located at an intersection of any two of the four segments.

In Example 31, the subject matter of any one or more of Examples 29-30 optionally include wherein one of the four segments is divided into two-sub-segments.

In Example 32, the subject matter of any one or more of Examples 21-31 optionally include wherein the strut comprises three segments that form a triangular pattern.

In Example 33, the subject matter of Example 32 optionally includes wherein the burr hole cover is located at an intersection of two of the three segments.

In Example 34, the subject matter of any one or more of Examples 32-33 optionally include wherein one of the three segments is divided into two-sub-segments.

In Example 35, the subject matter of any one or more of Examples 21-34 optionally include wherein the compound bone plate is one of a plurality of bone plate assemblies, each of the bone plate assemblies are different sizes.

In Example 36, the subject matter of any one or more of Examples 21-35 optionally include wherein the compound bone plate is one of a plurality of bone plate assemblies, wherein the plurality of plate members and the plurality burr hole covers for each of the plurality of bone plate assemblies has a different arrangement.

Example 37 is a method for performing a craniotomy, the method comprising: drilling at least one burr hole in a skull; cutting the skull at the burr hole to create a bone flap; removing the bone flap from the skull; attaching a first portion of a compound bone plate to the bone flap, the compound bone plate including a first plate member, a second plate member, a burr hole cover, and a strut connecting the first plate member, the second plate member, and the burr hole cover; placing the bone flap into an opening formed when the bone flap was removed from the skull; attaching a second portion of the compound bone plate to the skull.

In Example 38, the subject matter of Example 37 optionally includes using the compound bone plate as a stencil to create an outline of the bone flap on the skull.

In Example 39, the subject matter of any one or more of Examples 37-38 optionally include injecting a fill material through an opening defined by the burr hole cover to fill the burr hole.

In Example 40, the subject matter of any one or more of Examples 37-39 optionally include wherein attaching the first portion of the compound bone plate to the skull occurs after the bone flap is removed from the skull.

In Example 41, the subject matter of any one or more of Examples 37-40 optionally include wherein attaching the first portion of the compound bone plate to the skull occurs before placing the bone flap into the opening formed in the skull.

In Example 42, the subject matter of any one or more of Examples 37-41 optionally include wherein attaching the first portion of the compound bone plate to the skull occurs after placing the bone flap into the opening formed in the skull.

In Example 43, the compound bone plate, systems, or methods of any one of or any combination of Examples 1-42 are optionally configured such that all elements or options recited are available to use or select from.

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims.

What is claimed is:

1. A compound bone plate for attaching a bone flap to a skull and for use as a stencil, the compound bone plate comprising:
    a first plate member operable to be attached to the bone flap and the skull;
    a second plate member operable to be attached to the bone flap and the skull;
    a burr hole cover; and
    a strut connecting the first plate member, the second plate member, and the burr hole cover, the strut defining a notch that thins a portion of the strut.

2. The compound bone plate of claim 1, wherein the burr hole cover defines one or more through holes sized to allow a bone fill material to pass through the burr hole cover and into a burr hole formed in the skull.

3. The compound bone plate of claim 1, wherein the first plate member and the burr hole cover are integrated as a single component.

4. The compound bone plate of claim 1, wherein the strut is metallic and includes a polymer coating.

5. The compound bone plate of claim 1, wherein the first plate member comprises:
    a first prong operable to be attached to the bone flap;
    a second prong operable to be attached to the skull; and
    a third prong operable to be attached to the skull.

6. The compound bone plate of claim 1, wherein the strut orients the first plate member, the second plate member, and the burr hole cover in an asymmetric arrangement.

7. The compound bone plate of claim 1, wherein the strut orients the first plate member, the second plate member, and the burr hole cover in a symmetric arrangement.

8. The compound bone plate of claim 1, wherein the strut forms a circular or elliptical pattern.

9. The compound bone plate of claim 1, wherein the strut comprises four segments that form a rectangular pattern.

10. A compound bone plate for attaching a bone flap to a skull, the compound bone plate comprising:
    a plurality of plate members; each of the plurality of plate members operable to be attached to the bone flap and the skull;
    a plurality of burr hole covers; and
    a strut connecting the plurality of plate members and burr hole covers, the strut defining a plurality of notches that thin respective portions of the strut.

11. The compound bone plate of claim 10, wherein each of the burr hole covers defines one or more through holes sized to allow a bone fill material to pass through the burr hole cover and into a burr hole formed in the skull.

12. The compound bone plate of claim 10, wherein at least one of the plurality of plate members and at least one of the plurality of burr hole covers are integrated as a single component.

13. The compound bone plate of claim 10, wherein the strut is metallic and includes a polymer coating.

14. The compound bone plate of claim 10, wherein at least one of the plate members comprises:
    a first prong operable to be attached to the bone flap; and
    a second prong operable to be attached to the skull; and
    a third prong operable to be attached to the skull.

15. The compound bone plate of claim 10, wherein the strut orients the plurality of plate members and the plurality of burr hole covers in an asymmetric arrangement.

16. The compound bone plate of claim 10, wherein the strut orients the plurality of plate members and the plurality of burr hole covers in a symmetric arrangement.

17. The compound bone plate of claim 10, wherein the strut forms a circular or elliptical pattern.

18. The compound bone plate of claim 10, wherein the strut comprises four segments that form a rectangular pattern.

19. The compound bone plate of claim 18, wherein at least one of the plurality of burr hole covers is located at an intersection of any two of the four segments.

20. A method for performing a craniotomy, the method comprising:
    drilling at least one burr hole in a skull;
    cutting the skull at the burr hole to create a bone flap;
    removing the bone flap from the skull;
    attaching a first portion of a compound bone plate to the bone flap, the compound bone plate including a first plate member, a second plate member; a burr hole cover, and a strut connecting the first plate member, the second plate member, and the burr hole cover;
    cutting the strut at a notch defined by the strut;
    placing the bone flap into an opening formed when the bone flap was removed from the skull; and
    attaching a second portion of the compound bone plate to the skull.

* * * * *

UNITED STATES PATENT AND TRADEMARK OFFICE
CERTIFICATE OF CORRECTION

PATENT NO. : 11,457,955 B2
APPLICATION NO. : 16/874096
DATED : October 4, 2022
INVENTOR(S) : Garcia et al.

It is certified that error appears in the above-identified patent and that said Letters Patent is hereby corrected as shown below:

In the Claims

In Column 12, Line 13, in Claim 10, delete "members;" and insert --members,-- therefor In Column 12, Line 32, in Claim 14, after "flap;", delete "and"

In Column 12, Line 56, in Claim 20, delete "member;" and insert --member,-- therefor Signed and Sealed this
Twenty-second Day of November, 2022

Katherine Kelly Vidal
*Director of the United States Patent and Trademark Office*